(12) United States Patent
Scarpa et al.

(10) Patent No.: US 8,778,337 B2
(45) Date of Patent: Jul. 15, 2014

(54) USE OF S-ADENOSYLMETHIONINE (SAM) AND SUPEROXIDE DISMUTASE (SOD) FOR THE PREPARATION OF MEDICAMENTS FOR THE TREATMENT OF ALZHEIMER'S DISEASE

(75) Inventors: Sigfrido Scarpa, Rome (IT); Andrea Fuso, Pomezia (IT); Rosellina Damiani, Desio (IT); Mauro Rossini, Desio (IT)

(73) Assignee: Gnosis S.p.A., Milan (IT)

( * ) Notice: Subject to any disclaimer, the term of this patent is extended or adjusted under 35 U.S.C. 154(b) by 316 days.

(21) Appl. No.: 12/919,515

(22) PCT Filed: Feb. 25, 2009

(86) PCT No.: PCT/EP2009/001323
§ 371 (c)(1),
(2), (4) Date: Oct. 13, 2010

(87) PCT Pub. No.: WO2009/106302
PCT Pub. Date: Sep. 3, 2009

(65) Prior Publication Data
US 2011/0020301 A1  Jan. 27, 2011

(30) Foreign Application Priority Data
Feb. 29, 2008 (EP) ..................... 08425123

(51) Int. Cl.
*C12N 9/02* (2006.01)
(52) U.S. Cl.
CPC .................. *C12N 9/0089* (2013.01)
USPC ..................................... 424/94.4
(58) Field of Classification Search
CPC .................................. C12N 9/0089
USPC ..................... 514/17.8; 424/94.1
See application file for complete search history.

(56) References Cited

U.S. PATENT DOCUMENTS

| 5,519,058 A | 5/1996 | Gonick et al. |
| 6,759,395 B2 * | 7/2004 | Rao et al. ........................ 514/45 |
| 2002/0025926 A1 | 2/2002 | Herbert |
| 2003/0129261 A1 | 7/2003 | Henderson et al. |
| 2004/0048827 A1 * | 3/2004 | Scarpa et al. ................... 514/46 |
| 2006/0018839 A1 * | 1/2006 | Ieni et al. ....................... 424/45 |

FOREIGN PATENT DOCUMENTS

| EP | 1 731 596 | 12/2006 |
| WO | 99/17778 | 4/1999 |
| WO | 2005/041996 | 5/2005 |

OTHER PUBLICATIONS

Fuso, A. et al., "B-vitamin deprivation induces hyperhomocysteinemia and brain S-adenosylhomocysteine, depletes brain S-adenosylmethionine, and enhances PS1 and BACE expression and amyloid-beta deposition in mice" Molecular and Cellular Neuroscience, vol. 37, No. 4, Apr. 2008, pp. 731-746.
Fuso, A. et al., "gamma-Secretase is differentially modulated by alterations of homocysteine cycle in neuroblastoma and glioblastoma cells" Journal of Alzheimer's Disease, vol. 11, No. 3, Jun. 2007, pp. 275-290.
Scarpa, S. et al., "Gene silencing through methylation: an epigenetic intervention on Alzheimer's disease" Journal of Alzheimer's Disease, vol. 9, No. 4, Aug. 2006, pp. 407-414.
Scarpa, S. et al., "Presenilin 1 gene silencing by S-adenosylmethionine: a treatment for Alzheimer's disease?" FEBS Letters, vol. 541, No. 1-3, Apr. 24, 2003, pp. 145-148.
Database WPI Week 199722, Thomson Scientific, London GB.
Fuso, A. et al., "S-adenosylmethionine/homocysteine cycle alterations modify DNA methylation status with consequent deregulation of PS1 and BACE and beta-amyloid production" Molecular and Cellular Neuroscience, vol. 28, No. 1, Jan. 2005, pp. 195-204.

* cited by examiner

*Primary Examiner* — Ruth Davis
(74) *Attorney, Agent, or Firm* — Silvia Salvadori; Amin Talati, LLC

(57) ABSTRACT

The use of S-adenosylmethionine (SAM) in combination with superoxide dismutase (SOD) for the preparation of medicaments for the treatment of Alzheimer's disease.

3 Claims, 4 Drawing Sheets

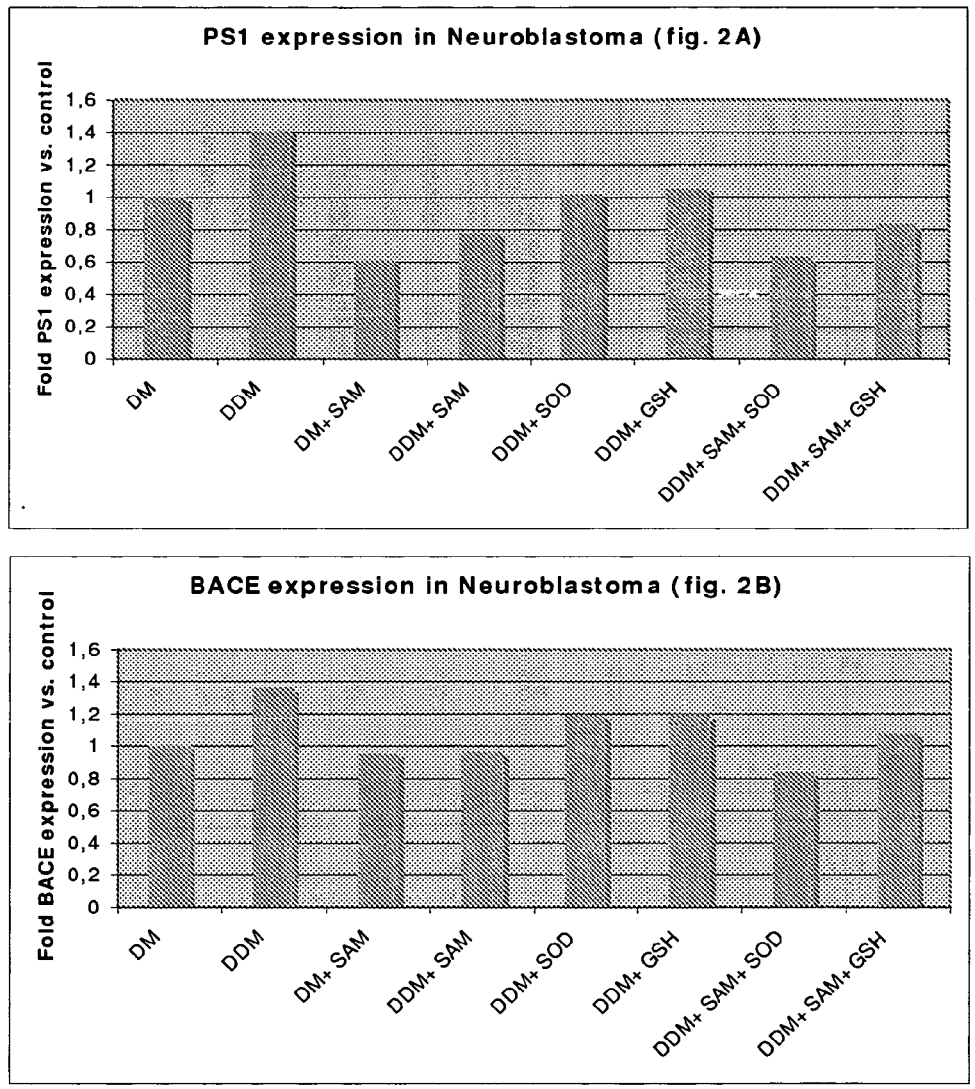

USE OF S-ADENOSYLMETHIONINE (SAM) AND SUPEROXIDE DISMUTASE (SOD) FOR THE PREPARATION OF MEDICAMENTS FOR THE TREATMENT OF ALZHEIMER'S DISEASE

This application is a U.S. national stage of PCT/EP2009/001323 on Feb. 25, 2009 which claims priority to and the benefit of European Application No. 08425123.0 filed on Feb. 29, 2008, the contents of which are incorporated herein by reference.

The present invention relates to the use of S-adenosylmethionine (SAM) in combination with superoxide dismutase (SOD) for the preparation of medicaments for the treatment of Alzheimer's disease.

BACKGROUND TO THE INVENTION

Alzheimer's disease (AD) is a very widespread neurodegenerative form of dementia which affects a high percentage of the world's population over 70 years old, with a ratio of 1:2 between men and women. The incidence of AD is constantly increasing, as the more common non-genetic form begins at around the age of 70-75, and life expectancy is increasing due to higher standards of living combined with the progress of medicine and pharmacology. The disease also exists as a genetically transmitted form associated with mutations in some loci of chromosomes 14, 19 and 21 (typical of persons suffering from Down's syndrome). Early onset of the familial form of AD takes place at around 50 years old, and causes brain degeneration followed by death in 2-3 years. The late-onset form of the disease also gives rise to brain degeneration and death, but in a period of 10 or more years.

The brain presents a large number of plaques in the inter-neuronal spaces and typical neurofibrillary tangles in the neurons, especially those of the cerebral cortex, hippocampus and amygdala, and in other parts of the brain with cognitive functions. Amyloid plaques, also known as senile plaques, are polymers of the peptide beta-amyloid (Aβ), which derives from a larger protein: beta-amyloid precursor protein (APP). APP is a member of the highly conserved superfamily of transmembrane glycoproteins.

In the last decade, numerous studies have been conducted by scientists engaged in research into AD with a view to understanding its etiology, especially as regards the molecular mechanisms. Research into the molecular components and their regulation can clarify their therapeutic and diagnostic prospects. Attention has focused on presenilins, whose role in processing APP, and therefore in producing Aβ, appears to be highly significant. It has been demonstrated that these proteins, presenilin 1 (PS1) and presenilin 2 (PS2), present an enzymatic activity or regulate the activities of other enzymes, namely secretases, which cleave APP into normally degradable catabolites (alpha-secretase) or into peptide Aβ (beta- and gamma-secretase). In familial AD, mutations of the genes coding for PS1 and PS2 lead to excessive production of Aβ and accumulation of isoform Aβ-42 in particular, which is highly amyloidogenic. Recently, experiments on PS1 knockout mice evidenced a great reduction in gamma-secretase activity, demonstrating that PS1, as well as belonging to the gamma-secretase complex, is also mainly responsible for the production and accumulation of Aβ. As regards beta-secretase, it is believed that the product of the BACE gene can perform beta-secretase cleavage alone.

The development of clinically useful gamma- and beta-secretase inhibitors could become a crucial weapon against Alzheimer's disease, and is currently one of the most exciting competitions in neuroscience. It has been clearly demonstrated that the activity of PS1 cannot be wholly suppressed, because this protein is needed to process transduction factor Notch-1, a crucial factor for the maturity of many stem cells, such as those involved in erythropoiesis.

Regulation of gene expression by means of DNA methylation can be successfully studied in a cell culture system able to express the genes involved in AD. As a result of our studies, a very interesting indication has been found in the regulatory mechanisms involved in aging, which consists of a gradual, global increase in DNA hypomethylation in the elderly, and homocysteine accumulation observed in patients suffering from senile dementia. Homocysteine accumulation and DNA hypomethylation are metabolically correlated, because the failure of homocysteine to be converted to methionine reverses the metabolism towards synthesis of S-adenosylhomocysteine, which is known to be a strong DNA-methyltransferase inhibitor, and therefore induces DNA hypomethylation. In accordance with the well-established theory that many genes are expressed when the cytosines of specific sequences are demethylated, this biochemical pattern can lead to expression of unexpressed genes and overexpression of normally expressed genes. This may be the case with AD, because the overexpression of PS1, namely gamma-secretase, may discontinuously exceed alpha-secretase activity, and therefore produce the peptide Aβ, which accumulates, and can cause the disease after many years. A further indication of the possible role of DNA methylation in AD is the finding that AD patients present much lower post mortem levels of methyl donors in the brain. Lower availability of S-adenosylmethionine (SAM) could easily lead to altered or increased expression of the genes involved in APP metabolism, eventually producing an accumulation of peptide Aβ in the senile plaques.

Preliminary experiments have been performed on a neuroblastoma line (SK-N-SH) which expresses APP, PS1, PS2, BACE, alpha-secretase, the other components of gamma-secretase, and Notch1. The cultures were treated with a culture medium deprived of folate, vitamin B12 and vitamin B6 (in order to alter the metabolism of homocysteine), to which SAM was added at various concentrations (to balance the effects of vitamin deprivation). We found an increase in PS1 and BACE expression in the vitamin B-deprived medium, and a marked reduction in PS1 and BACE expression after the administration of SAM. In experiments conducted with HpaII/PCR on APP and PS1 promoters, we found a major difference in the methylation of one of the CpG sites of the PS1 promoter. We concluded that the PS1 gene can be partly silenced by administration of exogenous SAM. The administration of SAM can reduce PS1 expression, restoring the metabolic balance in favour of alpha-secretase. Experiments have also been conducted with transgenic mice of the strain TgCRND8, and corresponding controls; these mice are characterised by the presence of the human mutated APP gene, and can therefore develop amyloid plaques in a short time. These animals were fed on a complete diet or a diet lacking in the vitamins of the B group; once again, as in the cells, an increase in PS1 and BACE expression was observed.

In both the experimental models, the alteration of gene expression had the effect of increasing gamma- and beta-secretase activities with consequent overproduction of Aβ, which accumulated to form senile plaques more rapidly than in the animals treated with the control diet.

The data summarised above have been reported in the following publications:

Fuso A., Nicolia V., Cavallaro R. A., Ricceri L., D'Anselmi F., Coluccia P., Calamandrei G. and Scarpa S. 2008. B-Vitamin Deprivation Induces Hyperhomocysteinemia and Brain S-adenosylhomocsyteine, Depletes Brain S-adenosylmethionine, and Enhances PS1 and BACE Expression and Amyloid-β Deposition in Mice. Mol. Cell. Neurosci. 37: 731-746.

Fuso A., Cavallaro R. A., Zampelli A., D'Anselmi F., Piscopo P., Confaloni A. and Scarpa S. 2007. γ-secretase is differentially modulated by alterations of Homocysteine cycle in neuroblastoma and glioblastoma cells. J. Alz. Dis. 11: 275-290.

Cavallaro R. A., Fuso A., D'Anselmi F. and Scarpa S. 2006. The effect of S-adenosylmethyonine on CNS gene expression studied by cDNA mycroarrays analysis. J. Alz. Disease. 9: 415-419.

Scarpa S., Cavallaro R. A., D'Anselmi F. and Fuso A. 2006. Gene silencing through methylation: an epigenetic intervention on Alzheimer Disease. J. Alz. Disease. 9: 407-414.

Fuso A., Seminara L., Cavallaro R. A., D'Anselmi F. and Scarpa S. 2004. Homocysteine/S-adenosylmethionine Cycle Alterations Unbalance DNA Methylation Status with Consequent Up-regulation of Beta-amyloid Prmnotinn. Mnl. cell. Nelirnri. 28(1):195-204.

Scarpa S., Fuso A., D'Anselmi F., Cavallaro R. A. 2003. Presenilin 1 gene silencing by S-adenosylmethionine: a treatment for Alzheimer disease? FEBS Letters 541 (1-3): 145-148.

Fuso A., Cavallaro R. A., Orrù L., Buttarelli F. R. and Scarpa S. 2001. Gene silencing by S-adenosylmethionine in muscle differentiation. FEBS Letters 508 (3): 337-340.

The use of SAM to treat AD was also proposed in US 2002/025926 and US 2004/0048827. The latter document demonstrated the ability of SAM to interfere with beta-secretase, presenilin 1 and 2 and beta-amyloid protein precursor gene expression. Studies conducted with labelled (tritiated) SAMe after said patent application demonstrated the ability of the molecule to reach the central nervous system after oral administration, as reported below.

The beneficial effect of SOD in the treatment of AD is suggested in U.S. Pat. No. 5,519,058 and in CN 1099224.

Pharmaceutical compositions comprising SAM and SOD together with a number of active ingredients, for use in conditions other than AD, are disclosed in US 2003/129261 and in WO 2005/041996.

DESCRIPTION OF THE INVENTION

It has now been found that the activity of S-adenosylmethionine can be surprisingly improved when it is administered in combination with superoxide dismutase (SOD). This enzyme has not only proved able to facilitate the passage of S-adenosylmethionine through the blood-brain barrier, but also interacts synergically with SAM in reducing the expression of the PS1 and BACE genes overexpressed as a result of vitamin B deficiency.

One aspect of the invention therefore relates to products containing S-adenosylmethionine or a derivative thereof and superoxide dismutase in the form of a combined preparation for simultaneous, separate or sequential administration in the treatment of Alzheimer's disease.

The doses can vary within a wide range in view of the very low toxicity of SAM and SOD, and will depend on a number of factors, such as the patient's weight, sex and age. However, broadly speaking, they will be between 200 and 2000 mg/day for SAM and between 50 and 1000 mg/day for SOD.

SAM can be administered, preferably orally, either as such or in the form of a stable salt thereof such as tosylate, butanedisulphonate, disulphate tosylate, disulphate ditosylate or disulphate monotosylate. An advantageous form of administration is *Saccharomyces cerevisiae* cells enriched with SAM, described in WO 2006/131382.

SOD, obtained by fermentation from strains of *Saccharomyces cerevisiae* as described in WO 2006/131382 filed by the Applicant, can also be administered orally, supported on gliadin film, or using other gastroprotection techniques. As an alternative to the oral route, both SAM and SOD can be administered parenterally, e.g. by intramuscular injection.

Examples of these formulations include tablets film-coated with acrylic or methacrylic polymers, gastroresistant capsules, microcapsules and the like.

SAM and SOD can be present in the same dose unit or formulated and administered separately: in that case, kits could be provided comprising the two drugs in separate dose forms accompanied by instructions for their sequential, simultaneous or separate use.

DESCRIPTION OF FIGURES

FIG. 2 shows the effect of SOD and glutathione (GSH) on the overexpression of PS1 and BACE in neuroblastoma cells of the line SK-N-BE, alone and in combination with SAM.

The invention will now be described in greater detail by means of the pharmacological tests described below by way of example.

EXAMPLE 1

Gene Expression

In particular, the effect of SAM was tested at pharmacological concentrations (400 μg/day) on TgCRND8 mice and the corresponding wild-type controls.

Gene Expression Channels

RNA was extracted from cell cultures and homogenised brains, and cDNA was synthesised. 0.5 μg of total cDNA was used for each real-time reaction on an Opticon2 DNA Engine (MJ Research) using SYBR-Green reagents. The amplification efficiency for each pair of primers was previously determined by amplification of a standard linear curve. The experimental samples were compared with a standard curve of a specific gene to determine the quantity of specific cDNA present in the standard reaction. The standards were obtained from highly purified PCR products amplified by positive controls. The total cDNA levels were normalised to the β-actin control (gene housekeeping).

Figure 1A:
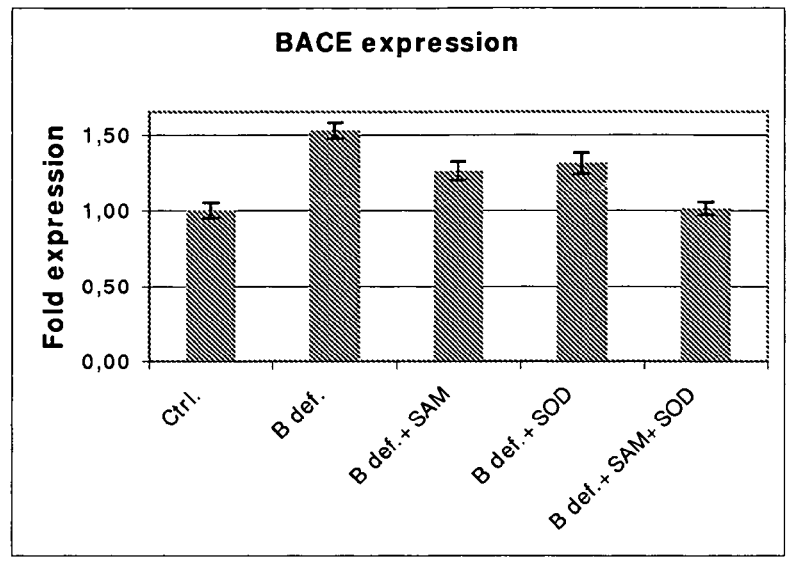
FIGS. 1a and 1b shows the effect of SAM and SOD in mice, on overexpression of PS1 and BACE induced by a vitamins B-deprived diet.
Figure 1B:
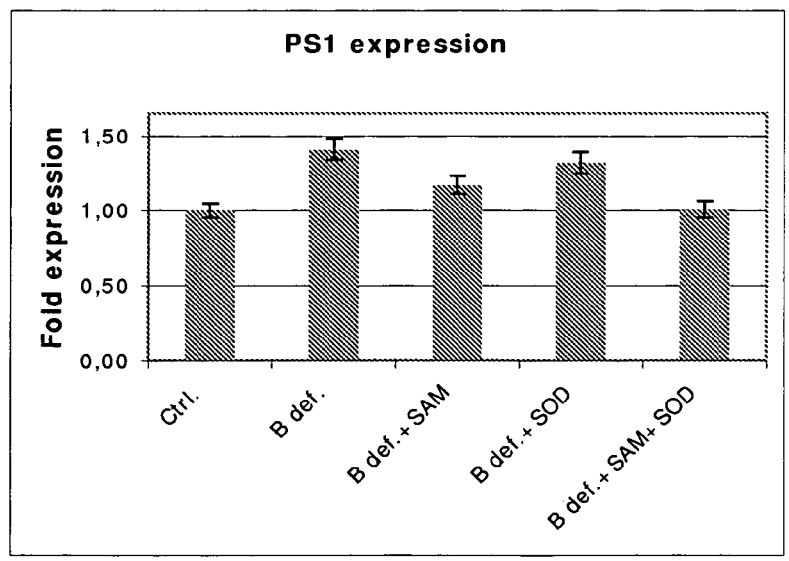

The results demonstrate that SAM also reverses the overexpression of PS1 and BACE induced by a deprived diet in vivo (FIG. 1), and even reduces it to lower levels than those of the control diet.

As homocysteine metabolism is involved in both methylation and oxidoreduction reactions, we tested the effect of various antioxidants on the expression of the two genes. The first data obtained with neuroblastoma cells of the SK-N-BE line demonstrated that both SOD and glutathione (GSH) inhibit overexpression of PS1 and BACE induced by vitamin deprivation, though to a lesser extent than SAM. However, it is interesting to note that when SOD and SAM are administered together, they present a synergic effect (FIG. 2) which further reduces the expression of the two genes to lower levels than those observed with SAM alone (15-20% less).

EXAMPLE 2

SAM Uptake

Experiments were conducted on cells and mice to demonstrate that SAM crosses the blood-brain barrier.

For the cell cultures, 100 μM of SAM was added to the F14 cell culture medium (complete or deprived of vitamin B, according to trial design) and the cultures were stopped after 96 hours.

For the mice, 400 μg/day of SAM was administered orally by feeding probe needle, and the animals were sacrificed after 2 months; the animals were fed on a complete diet or a vitamin B-deprived diet, according to trial design. SAM levels were analysed by HPLC with a Varian HPLC system. The cells and homogenised brains were lysed in distilled water, and the macromolecules were precipitated with 1.5 M PCA. Standard SAM curves were calculated before and after the experimental samples. For the analysis of tritiated SAM, cells were treated as described above, while mice were treated for 4 days to minimise exposure to the radioactive drug. The cells and homogenised brains were lysed in distilled water. A portion of lysed brains was sonicated and centrifuged to separate membranes and cell organelles; another portion was treated with perchloric acid (PCA) after sonication to separate the macromolecules. The uptake of radioactive SAM was measured by scintillation with a beta counter.

It was found that the intracellular levels of SAM increased from 1 (control) to 2.5-3 μM. To establish whether the increase was due to uptake of exogenous SAM as opposed to an increase in the endogenous reserves in the presence of elevated extracellular concentrations of the molecule, a test was performed with radioactive SAM. 100 μM of tritiated SAM (SAM[3H]) was added to SK-N-BE cell cultures, and the uptake was evaluated by cell lysis and radioactivity count. A radioactivity count of 1.5 μM of SAM in the cell lysates was found; this value is comparable to the increase from 1 to 2.5 times found with non-tritiated SAM, and clearly indicates that the intracellular increase is due to uptake of exogenous SAM.

Figure 3:
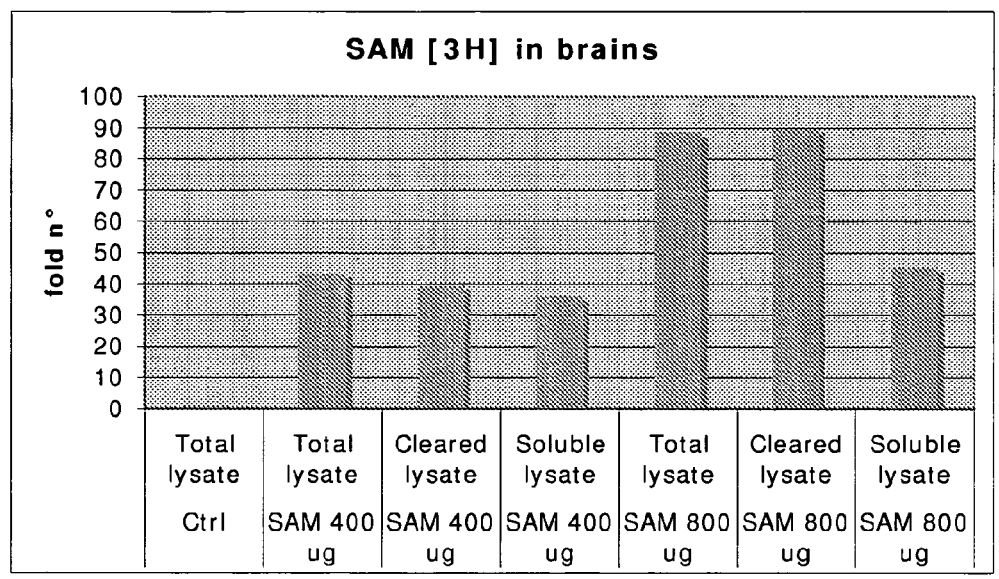
FIG. 3 shows the levels of tritiated SAM in the brains of mice after oral administration of SAM 400 μg/day.

A similar increase in SAM levels was found in brain lysates of mice treated orally with 400 μg/day of SAM; once again, a further test was performed with SAM[3H] at the concentration of 400 and 800 μg/day. The increased radioactivity in the total brain lysates is comparable to 0.5 ng of SAM per brain in mice treated with 400 μg of SAM, and 1 ng per brain in mice treated with 800 μg of SAM (FIG. 3).

A portion of the total brain lysates was also sonicated and centrifuged to obtain a cleared lysate (cytoplasm), and a further portion of this cleared lysate was precipitated with perchloric acid (PCA) to eliminate the proteins (soluble lysate). It is interesting to note that the soluble lysate from mice treated with 800 μg of SAM shows a radioactivity level comparable to 0.5 ng of SAM (whereas the total and cleared lysates presented higher levels), indicating that the excess methyl function bonded to exogenous SAM was conjugated with other cell molecules.

EXAMPLE 3

Amyloid production in Neuroblastoma Cell Lines

Methods: Media and Cell Cultures

Neuroblastoma SK-N-BE human cell line was maintained in F14 medium with 10% FCS and shifted to complete differentiation medium (control medium, with 1% FCS plus 10 μM retinoic acid) or to differentiation medium deficient of folate, vitamin B12 and vitamin B6 (B deficient). Cultures were re-fed every second day and stopped after 96.

Animals and Diets

At approximately 3 weeks of age, mice were systematically assigned to either a control diet group or to a deficient diet group, receiving food and water ad libitum. The control (AIN-93M; diet A: folate mg 1.98; Vitamin B12 mg 0.025; Vitamin B6 mg 7) and experimental diets (AIN-93M B; diet B, deficient in folate, vitamin B12 and vitamin B6) were purchased from Mucedola (Italy). Both diets contained 1% sulfathiazole to inhibit folate formation by means of gut bacteria and ensure that the only source of folate was the diet. Moreover, other three groups of animals received SAM (800 μg/day) or SOD (10 U/day) or the combination of both drugs (SAM 400 μg/day and SOD 5 U/day). After one week of treatment, mice were anesthetized and sacrificed to obtain brain and blood. Blood was collected by heart puncture in a test tube containing EDTA 2 g/dl and immediately centrifuged to separate the plasma and erythrocytes, then stored at −80° C. Brains were perfused with PBS and removed.

Amyloid Analysis

Homogenized brains were lysed with 50 mM TRIS-HCl pH 7.4, 150 mM NaCl, 0.2% Nonidet P-40, 1% CHAPS, 2 mM EDTA, PMSF (200 μM), Leupeptin (1 μM), Pepstatin A (1 μM) and Calpain Inhibitor I (5 μM). Protein extracts were used for ELISA test with Aβ 1-42 Immunoassay kit (BioSource International, Belgium); ELISA kit guarantee a good linear sensitivity until 10 pg/mL (1-42). All measurements were performed in triplicate.

Statistical Analysis

One-way ANOVA was computed and Bonferroni post test was used to evaluate any significant ($p<0.05$) difference reported.

Results

Figure 4:
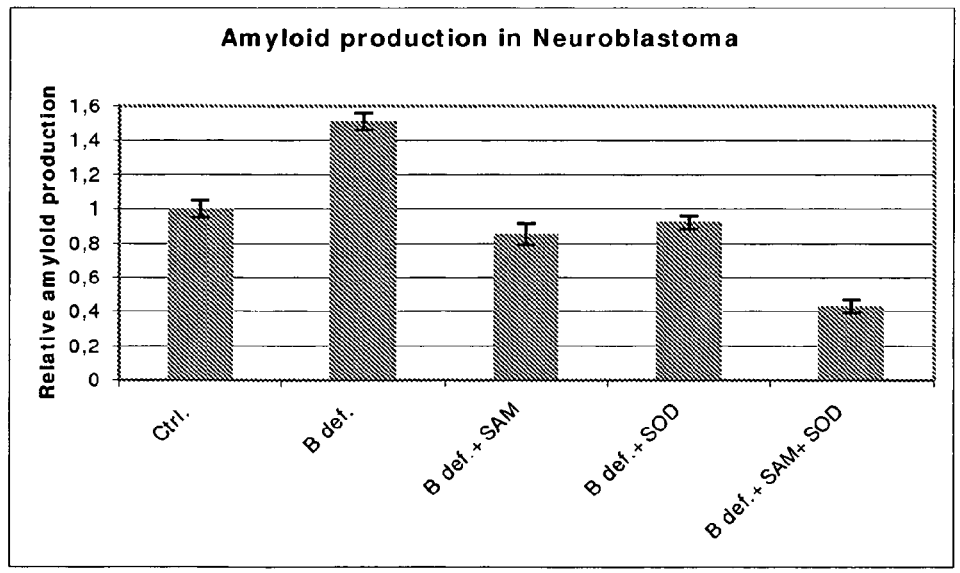
FIG. 4 shows the measure of amyloid-beta production in human Neuroblastoma cells after one week of treatment.
Figure 5:
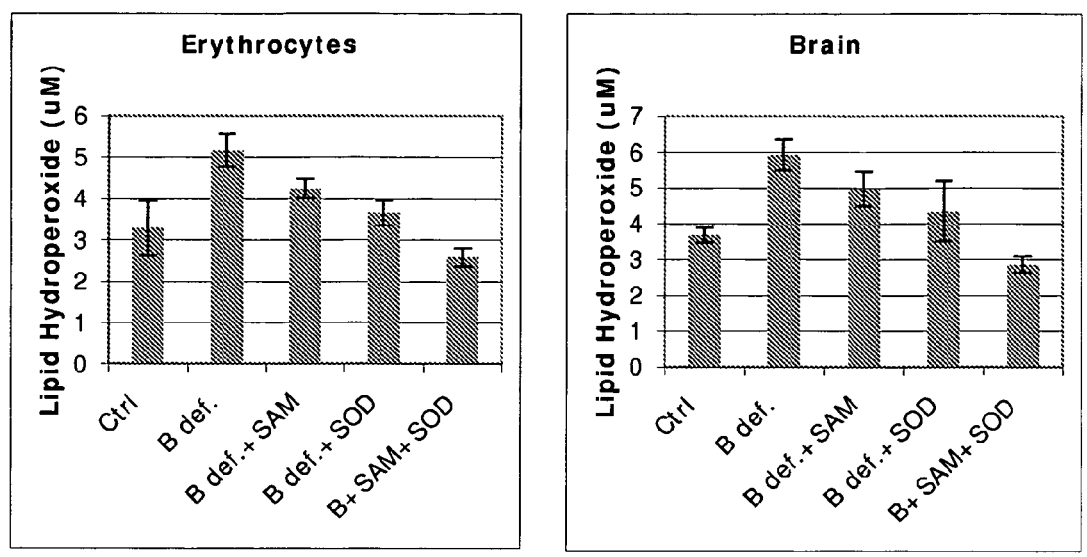
FIG. 5 shows the effect of SAM and SOD on oxidative status in eythrocytes and brain of mice treated with B-deprived diet.

From the data reported in FIG. 4, the synergy between SAM and SOD appears evident and confirmed by the statistical analysis reported below, always with reference to FIG. 4.

B def. vs. Ctrl: $p<0.001$
B def.+SAM and B def.+SOD vs. B def.: $p<0.001$
B def.+SAM+SOD vs. B def.: $p<0.001$
B def.+SAM+SOD vs. B def.+SAM and B def.+SOD: $p<0.001$

The invention claimed is:

1. A method of treatment for Alzheimer's disease comprising administering to a patient in need thereof an effective amount of medicaments comprising S-adenosylmethionine (SAM) in combination with superoxide dismutase (SOD) wherein said effective amount is a dose between 200 and 2000 mg/day for SAM and 50 and 1000 mg/day for SOD.

2. The method as claimed in claim 1, wherein the medicaments inhibit overexpression PS1 and BACE.

3. The method as claimed in claim 1, wherein the medicaments are administered orally.

* * * * *